United States Patent [19]

Oddell

[11] 4,107,563
[45] Aug. 15, 1978

[54] X-RAY GENERATING TUBES

[75] Inventor: Leonard George Oddell, Bognor Regis, England

[73] Assignee: EMI Limited, Hayes, England

[21] Appl. No.: 785,205

[22] Filed: Apr. 6, 1977

[30] Foreign Application Priority Data

Apr. 28, 1976 [GB] United Kingdom ............... 17203/76

[51] Int. Cl.$^2$ ............................................. H01J 35/10
[52] U.S. Cl. ....................................... 313/60; 313/149
[58] Field of Search ........................................... 313/60

[56] References Cited

U.S. PATENT DOCUMENTS 3,836,805  9/1974  Kok .......................................... 313/60

Primary Examiner—Rudolph V. Rolinec
Assistant Examiner—Darwin R. Hostetter
Attorney, Agent, or Firm—Cooper, Dunham, Clark, Griffin & Moran

[57] ABSTRACT

An X-ray generating tube is disclosed, which tube is especially suitable for use in a computerised tomographic apparatus in which a spread of x-radiation is required to shift rapidly relative to the body of a patient under examination. The tube contains a rotating anode which is either reciprocated to-and-fro along the axis of rotation thereof or contains a shaped profile which scans along said axis.

6 Claims, 2 Drawing Figures

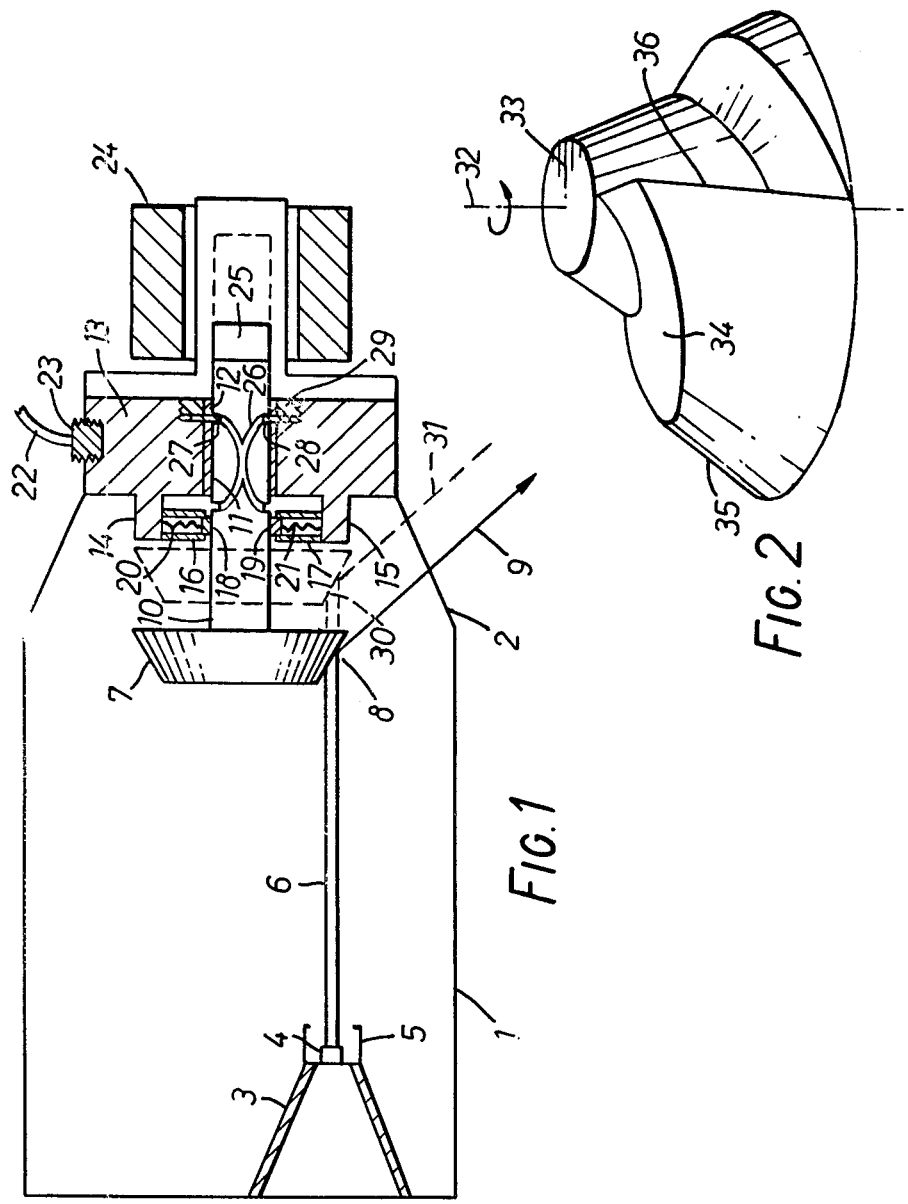

X-RAY GENERATING TUBES

The present invention relates to X-ray generating tubes, and it relates more especially to such tubes which have a rotating anode. The invention is especially, though not exclusively, concerned with providing an X-ray generating tube suitable for use in a computerised tomographic apparatus for examining cross-sectional slices of patients' bodies. Examples of computerised tomographic apparatus, and methods of operating such apparatus, are disclosed and claimed in U.S. Pat. No. 3,778,614.

In some circumstances, it is desirable for computerised tomographic apparatus to have a source which is capable of rapidly shifting a fan-shaped distribution from one place to another with respect to the patient being examined. It has been proposed to effect such shifting by electromagnetic or electrostatic deflection of the electron beam of the X-ray tube. United States patent application Ser. Nos. 559,715, 608,276 (now U.S. Pat. No. 4,002,917, granted Aug. 27, 1975), 630,779 (now U.S. Pat. No. 4,010,371, granted Nov. 11, 1975), 733,941 and 668,518 disclose various computerised tomographic arrangements in which such electron beam deflection is used to shift radiation laterally across the examined slice of a patient's body, longitudinally of said slice, or to hold the radiation in a certain disposition relative to the patient despite physical rotation of the X-ray tube around the patient.

In U.S. patent application Ser. No. 733,220 there is described an X-ray tube having a rotating anode and in which said anode has a surface form rotatable about an axis to vary the point in space at which the electron beam impinges on said anode, thereby to scan the X-radiation along a selected path, without the need for electrostatic or electromagnetic deflection of the electron beam of the tube. As specifically described, the anode, which is basically disc-shaped, is rotated about an axis perpendicular to the anode and the electron beam impinges on the surface of the disc, which surface is formed to move, in space, the point at which the electron beam impinges so as to produce a scan of the resulting X-ray radiation in a direction substantially perpendicular to the axis of rotation.

It is an object of this invention to provide an X-ray generating tube without electrostatic or electromagnetic beam deflection, which can produce a scan in a direction other than that perpendicular to the axis about which the anode rotates.

According to the invention there is provided an X-ray generating tube including an anode rotatable about an axis, an electron beam source for projecting an electron beam towards said anode so as to impinge upon a region thereof, and means for reciprocating said region in a direction substantially parallel to said axis.

In order that the invention may be clearly understood and readily carried into effect, some embodiments thereof will now be described, by way of example only, with reference to the accompanying drawings in which:

FIG. 1 shows an outline cross-section of an X-ray generating tube in accordance with one example of the invention, and FIG. 2 shows a perspective view of an anode suitable for incorporation in an X-ray generating tube, according to another aspect of the invention.

The tube shown in FIG. 1 has an evacuated envelope 1, which may be of copper or glass, for example, and which is formed at 2 with an exit window for X-radiation. The window 2 may be of different material than the material of which the remainder of the envelope 1 is constructed. An electrically insulating support 3 is secured to the envelope 1 and supports a cathode 4 and a control electrode 5 which is disposed adjacent the cathode 4 so that it can act as a guard plate, focus electrode or control grid for said cathode, depending upon the potential applied thereto. No means are shown for applying potentials to the cathode 4 or the electrode 5 as such means are well known and may be entirely conventional, and form no part of this invention. In any event, the cathode 4 produces an electron beam 6, usually of ribbon shape, although the beam 6 may take other forms, such as circular cross-section, if desired. The beam 6 is projected towards a rotating anode 7 and impinges on a region such as 8 thereof. The anode 7 has a bevelled edge, as is usual and, in response to the impingement of the electron beam 6 thereon, emits X-radiation in a mean direction 9. The X-radiation is emitted in the form of a fan-shaped spread which extends perpendicular to the plane of the paper; the line 9 representing the median line of the spread.

The anode 7 is supported on a shaft 10 which rotates in a two-part bearing 11, 12 formed in an anode support and bearing block 13 formed of electrically conductive material such as copper. The block 13 has a pair of brush-holder supports 14 and 15 secured thereto, and each support holds a respective brush holder 16, 17. Brushes 18, 19 which are retained by the respective brush holders are resiliently urged into contact with the shaft 10 by means indicated schematically as springs 20, 21. The shaft 10, like the anode 7, is formed of copper (although the anode 7 is formed with the usual surface layer of X-ray emissive material) and thus electrical connection is established between the block 13 and the anode 7. Potential for the anode 7 can thus be applied by way of a lead 22 connected to a copper plug 23 screwed into the block 13 through an aperture in the envelope 1.

In accordance with this example of the invention, the anode is not only rotated, by inductive co-operation between a stator 24 and a rotor 25, but also reciprocated along the direction of its axis of rotation.

The reciprocal motion of anode 7 is obtained by providing a continuous figure-of-eight groove 26 around shaft 10. Pegs 27, 28 engage the groove 26 and, in operation, the engagement of the pegs with the groove 26 produces the required reciprocal motion of the anode 7. As previously mentioned, the bearing in which the shaft 10 rotates and reciprocates is in two parts 11 and 12. Part 11 is fixed to block 13, whereas part 12 is formed on the inside of a threaded sleeve 29 which can be screwed into a threaded opening in the block 13 to trap a split-ring bearing the pegs 28, 29.

In operation, the electron beam 6 is directed toward the anode 7 to impinge on a region of its sloping surface. As the anode 7 rotates and reciprocates, the point in space at which the beam impinges upon the anode moves progressively from position 8 to another extreme position 30 and back. As the direction of X-radiation generated by the impact of an electron beam depends mainly on the beam energy, the X-radiation emergent through window 2 will shift in a substantially parallel manner between line 9 and a line 31 which represents the median line of the spread in the other extreme axial position of anode 7. In this way the radiation is scanned in a direction substantially parallel to the axis of rotation of the anode.

FIG. 2 shows an anode 33, suitable for incorporation in a tube according to another example of the invention, and having an axis of rotation 32. The anode 33 has a surface track 34 of substantially helical form provided thereon, and may be further modified as shown at 35 to a conical form. When an anode such as 33 is rotated, without reciprocation, in a tube such as that shown in FIG. 1 the region thereof upon which the electron beam 6 impinges is again moved in space in a sense causing the radiation to scan in a direction parallel to the axis of rotation of the anode. Instead of a contoured solid body as shown in FIG. 2 the surface track 34 may be provided by a contoured flange, subject to heat dissipation problems.

In either event, the resultant scan is rather in the form of a sawtooth motion, having a rapid flyback caused by the sharpness of angle of a junction portion 36 between the two ends of the surface track 34. If a continuous scan, rather than the aforementioned sawtooth form, is required the junction portion 36 can be modified accordingly so that the surface 34, 36 conforms to a continuous curve rather than the discontinuous one shown.

What I claim is:

1. An x-ray generating tube having an envelope and including an anode rotatable about an axis, an electron beam source for projecting an electron beam towards said anode so as to impinge thereon at a location within the tube and produce x-radiation originating at said location, and means for reciprocating the location of the origin of the x-radiation, on the anode, relative to the envelope and in a direction substantially parallel to said axis.

2. A tube according to claim 1 wherein said means for reciprocating comprise means for reciprocating said anode as a whole in said direction.

3. A tube according to claim 2 wherein said means for reciprocating comprise a shaft supporting said anode and a bearing block supporting said shaft for rotation about said axis, a figure-of-eight shaped groove formed in said shaft and a pair of pegs fixedly secured to said block so as to engage in said groove.

4. A tube according to claim 1 wherein said anode includes a track extending in substantially helical form along said anode in said direction, said location at which said electron beam impinges upon said anode being constrained to fall upon said track.

5. An x-ray generating tube having an envelope and including an anode rotatable about an axis, means for producing an electron beam impinging on said anode at a location within the tube and causing said anode to emit x-radiation propagating out of the envelope from said location and means for selectively moving the location of the origin of the x-radiation on the anode, relative to the tube envelope, along a path which is not normal to the axis of rotation of the anode.

6. An x-ray generating tube having an envelope and including: an anode rotatable about an axis; an electron beam source for projecting an electron beam towards said anode; and means disposing the source relative to the envelope and means for moving the anode operative in combination so that the location within the envelope, at which the electron beam intercepts the anode surface and from which the generated x-rays originate, is movable in relation to said envelope along a locus substantially parallel to said axis.